United States Patent [19]
Appleby

[11] Patent Number: 5,908,430
[45] Date of Patent: Jun. 1, 1999

[54] EASY LOADING HEMOSTATIC CLIP AND CARTRIDGE

[76] Inventor: Timothy Appleby, 105 Willesden Dr., Cary, N.C. 27513

[21] Appl. No.: 08/821,780

[22] Filed: Mar. 20, 1997

Related U.S. Application Data

[63] Continuation of application No. 08/472,186, Jun. 7, 1995, abandoned.

[51] Int. Cl.⁶ ..................................................... A61B 17/04
[52] U.S. Cl. ......................... 606/157; 206/339; 206/340
[58] Field of Search ..................................... 206/338–341, 206/438; 227/902; 606/157, 158

[56] References Cited

U.S. PATENT DOCUMENTS

| | | |
|---|---|---|
| 4,076,120 | 2/1978 | Carroll et al. .......................... 206/340 |
| 4,696,396 | 9/1987 | Samuels . |
| 4,936,447 | 6/1990 | Peiffer ..................................... 206/340 |
| 4,961,499 | 10/1990 | Kulp . |
| 5,201,416 | 4/1993 | Taylor . |
| 5,484,362 | 1/1996 | Skowronski et al. ..................... 482/54 |
| 5,487,746 | 1/1996 | Yu et al. .................................. 606/151 |

*Primary Examiner*—Gary Jackson
*Attorney, Agent, or Firm*—Mills Law Firm PLLC

[57] ABSTRACT

The present invention provides a cartridge that retains clips in their slots and also facilitates removal of the clips by a clip applier. The slots are provided with at least one and preferably two retaining members that protrude from and preferably run substantially parallel to the slot-defining walls. The retaining members interfere with the clip to an extent sufficient to retain the clip in the slot while permitting relative movement between the clip and the saddle. In a preferred embodiment, the legs of the clip are flared to further facilitate engagement between the clip legs and the grooves of the applier jaws.

23 Claims, 2 Drawing Sheets

EASY LOADING HEMOSTATIC CLIP AND CARTRIDGE

This application is a continuation of application Ser. No. 08/472,186 filed Jun. 7, 1995, now abandoned.

FIELD OF THE INVENTION

The present invention relates to an improved clip and cartridge for holding and dispensing preformed, preferably flared, V-shaped hemostatic clips for occluding blood vessels during surgery.

BACKGROUND OF THE INVENTION

Hemostatic clips provide a rapid and efficient means for closing off blood vessels during surgery. Hemostatic clips generally are V-shaped and formed from a soft, biocompatible metal. Typically, hemostatic clips are supplied in a molded cartridge with multiple clip-containing slots. The clips are removed from their slots individually, when needed, by a clip applier. A typical clip applier has a pair of relatively movable jaws with grooves to receive the legs of the clip.

When pressed into a slot in the cartridge, the clip applier automatically grips the clip securely so that the clip can be removed from the slot and held by the applier. The applier then is used to position the V-shaped clip over a blood vessel and to compress the legs of the clip together so that the blood vessel is closed off. Afterward, the applier is disengaged from the clip and may be used to remove another clip from the cartridge.

In the past, cartridges have been designed to hold the clips relatively securely in their slots to guard against accidental release of the clips. The structures that have been used to secure clips in their slots typically have not permitted much movement of the clip within the slot. Typically, the legs of the clip are straddled and tightly fit over a "saddle." The clip often is retained on the saddle by a retaining member designed to abut the upper edge of the clip, holding the clip tightly in place on the saddle.

Unfortunately, the features used in the past to retain the clips in their slots also have made it difficult to remove the clips from their slots with an applier. A structure that would hold clips securely in their slots, but would also permit easy removal of the clips by an applier, would be highly desirable.

SUMMARY OF THE INVENTION

The present invention provides a cartridge that retains clips in their slots and also facilitates removal of the clips by a clip applier. The slots are provided with at least one retaining member protruding from at least one face of the slot-defining walls. The retaining member interferes with the clip to an extent sufficient to retain the clip in the slot while permitting relative movement between the clip and the saddle.

DETAILED DESCRIPTION OF THE INVENTION

Figure 1:
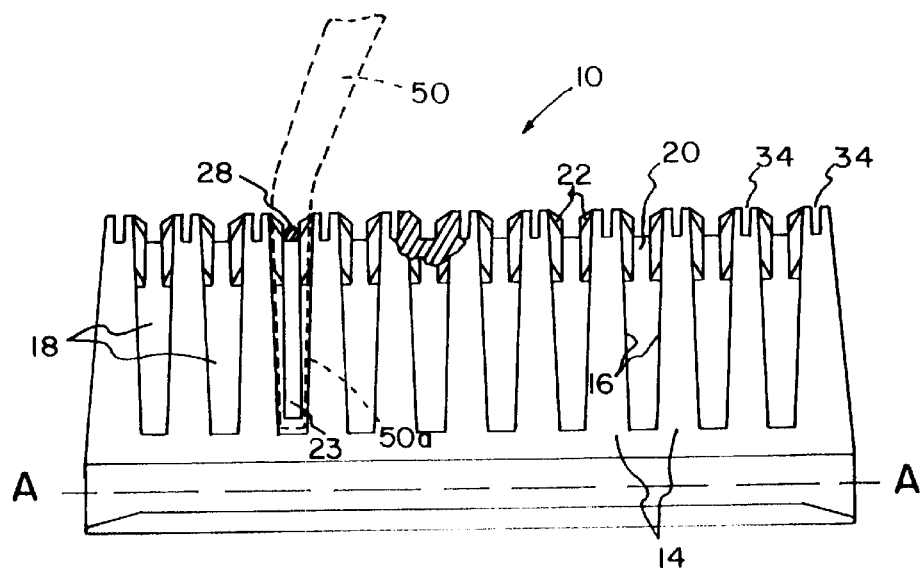
FIG. 1 is a prospective side view of a cartridge showing a clip applier engaging a hemostatic clip according to the present invention.

The cartridge 10 of the present invention, shown in FIG. 1, preferably comprises a unitary molded body with (a) an elongated base 12 having a longitudinal axis A—A; (b) a plurality of parallel walls 14 extending from the base 12 with faces 16 extending transverse to the longitudinal axis of the base and spaced to define a series of clip-receiving slots 18 between adjacent parallel walls 14; (c) a saddle 20 in each slot 18 adapted to support a clip; and (d) at least one retaining member 22 extending from an upper edge of at least one face of each slot.

The cartridge 10 may have any number of slots 18. FIG. 1 shows only a part of the total number of slots 18 in the cartridge 10 The cartridge 10 preferably is made of a low durometer elastomer to provide maximum flexibility and minimal frictional resistance between the clip and cartridge during clip removal. The durometer of the elastomer preferably should be in the range of about 40–55 Shore D. Each wall 14 preferably has a centrally located, substantially vertical slot 34 therethrough to provide the wall 14 with a degree of compressibility.

The cartridge 10 preferably should be disposable, and the cartridge material preferably should withstand steam sterilization without deforming. A preferred material for the cartridge is KRATON®, which is a styrenic thermoplastic elastomer available from Shell Chemical Co. KRATON® is a preferred material because it has a desirable durometer (35–55 shore A), and because it adheres to double-faced tape. Preattached double-faced tape applied to the bottom of the cartridge allows the user to secure the cartridge to a working surface and thereby remove the clips from the cartridge without the need to use a second hand to hold the cartridge.

Figure 2:
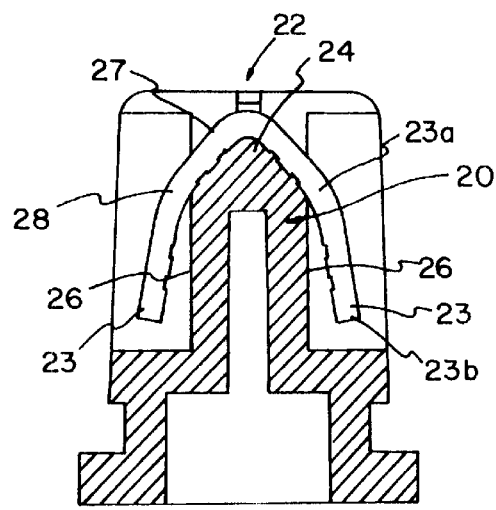
FIG. 2 is a cross sectional view through a slot of the cartridge of FIG. 1 showing a clip mounted on a saddle.

Each cartridge 10 may be provided in several different sizes in order to allow the surgeon to select a cartridge 10 containing the desired number and size of clips. The cartridge 10 of the present invention is intended to hold and dispense preformed, generally V-shaped hemostatic clips. An example of a preferred clip 28 is shown in FIG. 2. Preferred clip 28 has a pair of legs 23 with first and second regions 23a, 23b, respectively, and a connecting portion 27 extending between the first regions 23a of legs 23. As shown in FIG. 2, each of the second regions extends from a respective first region at an angle such that the second regions are not compressed when the clips are installed in the cartridge. As shown in FIG. 2, this angle is obtuse in a preferred embodiment. The clip is formed of soft, biocompatible metal, preferably titanium, tantalum, or stainless steel, and is adapted to be applied to a blood vessel by means of a clip applier. An example of a suitable clip applier 50 as shown in phantom outline in FIG. 1 is shown in U.S. Pat. No. 3,326,216 to Wood, incorporated herein by reference In a preferred embodiment, the clip applier should have open-ended rather than blind grooves.

The second regions 23b of the legs 23 of the clip 28 preferably are flared, rendering the clip 28 more "V"-shaped. Flaring of the clip legs 23 permits looser engagement between the clip 28 and the saddle 20 and reduces frictional resistance when the clip 28 is removed from the saddle 20. In a preferred embodiment, the saddle 20 is sufficiently narrow to allow free release of the clip 28 from the saddle 20 when the applier 50 pulls the clip 28 from the slot 18. A total clearance of at least 0.05 cm (0.01) between the inside surface of the clip legs 23 and the outer surface of the saddle 20 during removal of the clip 28 from the cartridge is preferred, regardless of clip size As seen in FIG. 2, the retaining members 22 preferably are substantially parallel. The retaining members 22 closely abut and actually interfere with the clip 28 at the "pinch point." The pinch point 40 is shown in cross section in FIG. 3. In a preferred embodiment, as shown in FIG. 3, two parallel retaining members 22 are provided The nominal interference between each clip edge 38 and the abutting retaining member 22 should be between about 0.0051–0.025 cm (0.002–0.01"), preferably 0.0127 cm (0.004").

Figure 3:
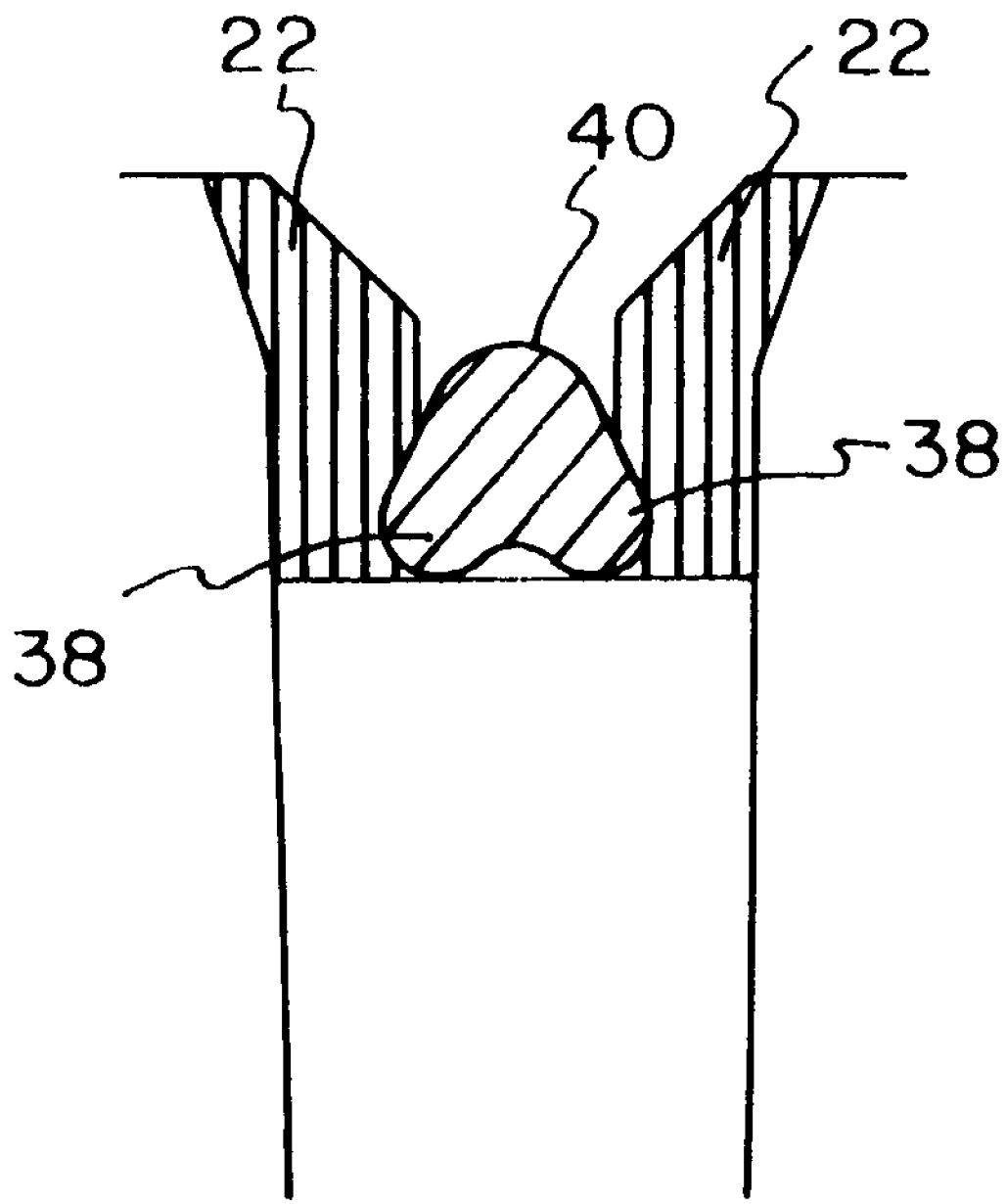
FIG. 3 is a cross sectional view through the pinch point of the clip shown in FIGS. 2.

The interference between the clip 28 and the retaining member(s) 22 retains the clip tightly within the slot 18 and over the saddle 20 until the legs 23 of the clip 28 are engaged by the clip applier, and the applier 50 as shown in FIG. 1 exerts sufficient pressure on the clip legs 23 to dislodge the apex 40 of the clip 28 from between the retaining member(s) 22 at the pinch point as most clearly seen in FIG. 3.

When the clip applier 50 is inserted into the slot 18, the pressure of the applier jaws 50a against the cartridge walls 14 compresses the relatively low durometer walls, thereby pulling the retaining member(s) away from the clip 28. This reduces the interference between the clip edges 38 and the retaining member(s) 22 and allows the clip 28 to be removed from the slot 18A.

The slots 18 should be larger than the clips 28, to allow sufficient clearance to insert the applier jaws 50a and to align the grooves (not shown) of the jaws 50a with the legs 23 of the clips 28. As shown in FIG. 1, the clearance between the faces 16 of the transverse walls 14 and the clearance between the lower regions 23b of the clip legs and the faces 16 of walls 14 is sufficient that the applier jaws (not shown) may be fully inserted into slot 18 to engage a clip 28 without contacting the opposed wall faces 16 forming the slot 18.

Persons of skill in the art will appreciate that many modifications may be made to the embodiments described herein without departing from the spirit of the present invention Accordingly, the embodiments described herein are illustrative only and are not intended to limit the scope of the present invention.

I claim:

1. A hemostatic clip application system for dispensing and applying preformed, generally V-shaped hemostatic clips to a blood vessel, said system comprising:

at least one clip comprising a pair of legs having first and second regions and a connecting portion extending therebetween and connecting said first regions of said legs;

a cartridge body base having a longitudinal axis;

a cartridge body comprising a plurality of substantially parallel walls extending upwardly from said base and substantially transverse to said longitudinal axis, said walls being spaced apart and having first and second substantially parallel, opposed wall faces defining slots to retain said clip, said slots including a saddle extending between said faces for mounting said clip within said slot and being adapted to permit relative movement of said clip with respect to said saddle, said saddle being configured and dimensioned to closely conform to an inner peripheral edge of said clip adjacent said first regions and said connecting portion thereof;

at least one retaining member protruding from said faces defining said slot, said retaining member interfering with said clip at a pinch point located on an apex thereof to an extent sufficient to hold said clip in said slot while permitting relative movement between said clip and said saddle, said clip being disposed on said saddle such that the clearance between said lower regions of said clip legs and said walls of said slots is of a predetermined dimension; and a clip applier for application of said clip about said blood vessel, said clip applier including a pair of opposed, articulating jaws formed thereon, said jaws having a pair of opposed grooves formed therein to grasp and withdraw said clip from said slots within said cartridge body, said jaws being configured to be insertable between said wall faces defining said slots to withdraw said clip without contacting said wall faces thereby eliminating any interference between said jaws and said wall faces to facilitate removal of said clip.

2. The clip application system of claim 1 wherein said second regions of said clip legs are flared.

3. The clip application system of claim 2 wherein said cartridge body is a unitary molded cartridge body.

4. The clip application system of claim 2 wherein said cartridge body comprises a low durometer material.

5. The clip application system of claim 4 wherein said extent of interference between said retaining member and said clip is between about 0.0051–0.025 cm (0.002–0.010").

6. The clip application system of claim 5 wherein said saddle has an outer surface and said clip legs have an inner surface that is separated from said outer surface of said saddle by a total clearance of at least about 0.05 cm (0.010").

7. The clip application system of claim 4 wherein said saddle has an outer surface and said clip legs have an inner surface that is separated from said outer surface of said saddle by a total clearance of at least about 0.05 cm (0.010").

8. The clip application system of claim 4 wherein said material has exceptional characteristics for adherence to adhesive tape.

9. The clip application system of claim 2 wherein said extent of interference between said retaining member and said clip is between about 0.0051–0.025 cm (0.002–0.010").

10. The clip application system of claim 9 wherein said saddle has an outer surface and said clip legs have an inner surface that is separated from said outer surface of said saddle by a total clearance of at least about 0.05 cm (0.010").

11. The clip application system of claim 2 wherein said saddle has an outer surface and said clip legs have an inner surface that is separated from said outer surface of said saddle by a total clearance of at least about 0.05 cm (0.010).

12. The clip application system of claim 1 wherein said cartridge body is a unitary molded cartridge body.

13. The clip application system of claim 12 wherein said cartridge body comprises a low durometer material.

14. The clip application system of claim 13 wherein said material has exceptional characteristics for adherence to adhesive tape.

15. The clip application system of claim 1 wherein said cartridge body comprises a low durometer material.

16. The clip application system of claim 15 wherein said material has exceptional characteristics for adherence to adhesive tape.

17. The clip application system of claim 15 wherein said extent of interference between said retaining member and said clip is between about 0.0051–0.025 cm (0.002–0.010").

18. The clip application system of claim 17 wherein said saddle has an outer surface and said clip legs have an inner surface that is separated from said outer surface of said saddle by a total clearance of at least about 0.05 cm (0.010").

19. The clip application system of claim 15 wherein said saddle has an outer surface and said clip legs have an inner surface that is separated from said outer surface of said saddle by a total clearance of at least about 0.05 cm (0.010").

20. The clip application system of claim 1 wherein said extent of interference between said retaining member and said clip is between,/about 0.0051–0.025 cm (0.002–0.010").

21. The clip application system of claim 20 wherein said saddle has an outer surface and said clip legs have an inner surface that is separated from said outer surface of said saddle by a total clearance of at least about 0.05 cm (0.010").

22. The clip application system of claim 1 wherein said saddle has an outer surface and said clip legs have an inner surface that is separated from said outer surface of said saddle by a total clearance of at least about 0.05 cm (0.010").

23. An improved clip application system for holding and dispensing pre-formed, generally V-shaped hemostatic clips, said clip application system being of the type including at least one clip comprising a pair of legs having first and second regions and a connecting portion extending therebetween and connecting said first regions of said legs, a cartridge body base having a longitudinal axis, a cartridge body including a plurality of substantially parallel walls extending upwardly from said base and substantially transverse to said longitudinal axis, said walls being spaced apart and having first and second substantially parallel, opposed wall faces defining slots therebetween to retain said clips therein, said improvements comprising:

saddle means interposed between said opposed wall faces within said slots, said saddle means being adapted to receive said clips in sliding engagement thereon, said saddle means being configured and dimensioned to closely conform to an inner peripheral edge of said clips adjacent said first regions and said connection portion such that said clips are secured in functional relation to said saddle while permitting relative movement between said clip and said saddle means to facilitate withdrawal thereof by a clip applier; and at least one retaining member protruding from said faces defining said slot, said retaining member interfering with said clip at a pinch point located on said connection portion to an extent sufficient to hold said clip in said slot while permitting relative movement between said clip and said saddle, said clip being disposed on said saddle such that the clearance between said lower regions of said clip legs and said opposed wall faces of said slot is of a sufficient dimension to permit said clip applier to be filly inserted into said slot without touching said faces of said slot.

* * * * *